(12) United States Patent
Albrektsson et al.

(10) Patent No.: US 6,503,255 B1
(45) Date of Patent: *Jan. 7, 2003

(54) CUTTING GUIDE INSTRUMENT (75) Inventors: Björn Albrektsson, Onsala (SE); Lars Carlsson, Kullavik (SE); Magnus Jacobsson, Göteborg (SE); Tord Röstlund, Kullavik (SE); Stig Wennberg, Angered (SE)

(73) Assignee: Astra Aktiebolag, Sodertalje (SE)

( * ) Notice: Subject to any disclaimer, the term of this patent is extended or adjusted under 35 U.S.C. 154(b) by 196 days.

This patent is subject to a terminal disclaimer.

(21) Appl. No.: 09/645,296

(22) Filed: Aug. 24, 2000

Related U.S. Application Data (63) Continuation of application No. 08/669,497, filed as application No. PCT/SE96/00489 on Apr. 17, 1996, now Pat. No. 6,120,510.

(30) Foreign Application Priority Data

May 17, 1995 (SE) ................................................ 9501828

(51) Int. Cl.[7] .............................................. A61B 17/58
(52) U.S. Cl. ......................................................... 606/89
(58) Field of Search .............................. 606/96, 87, 88, 606/89, 80, 82, 79, 102

(56) References Cited

U.S. PATENT DOCUMENTS 4,959,066 A * 9/1990 Dunn et al.
5,578,037 A * 11/1996 Sanders et al. ............... 606/80

* cited by examiner

Primary Examiner—Nicholas D. Lucchesi
Assistant Examiner—Melba Bumgarner
(74) Attorney, Agent, or Firm—White & Case LLP (57) ABSTRACT The invention relates to a cutting guide instrument and method for enabling high-precision resection of the head (caput femoris) (8) of the neck (5) of a human femur (collum femoris) at a predetermined cutting angle ($\alpha_c$) to the femoral shaft (9) and on a predetermined cutting level ($L_c$) with respect to the proximal end of the caput (8). A support part (11) is fixed to the femur during the resection. A longitudinal guide carrier (12) is supported by the support part (11) and is aligned along the femoral collum (5) at said predetermined cutting angle ($\alpha_c$) to the femoral shaft (9). A cutting guide (13) is supported by and movable along the axis (D—D) of the guide carrier (12) to a cutting position corresponding to the predetermined cutting level ($L_c$). The invention also relates to the use of the instrument for performing such resection.

12 Claims, 6 Drawing Sheets

Fig. 1

Prior art

CUTTING GUIDE INSTRUMENT

This application is a continuation of application Ser. No. 08/669,497 filed on Jul. 10, 1996, now U.S. Pat. No. 6,120,510, which is the National Stage of International Application PCT/SE96/00489, filed Apr. 17, 1996.

TECHNICAL FIELD OF THE INVENTION

The invention is usable in the field of hip joint prostheses for permanent anchoring in the human hip joint. More specifically, the invention relates to a cutting or sawing guide instrument for enabling high-precision resection of the head (caput) of the neck of a human femur (collum femoris) at a predetermined angle to the femoral shaft and on a predetermined level with respect to the proximal end of the caput. The invention also relates to the use of such an instrument, as well as a method for enabling such high-precision resection.

BACKGROUND ART

Figure 1:
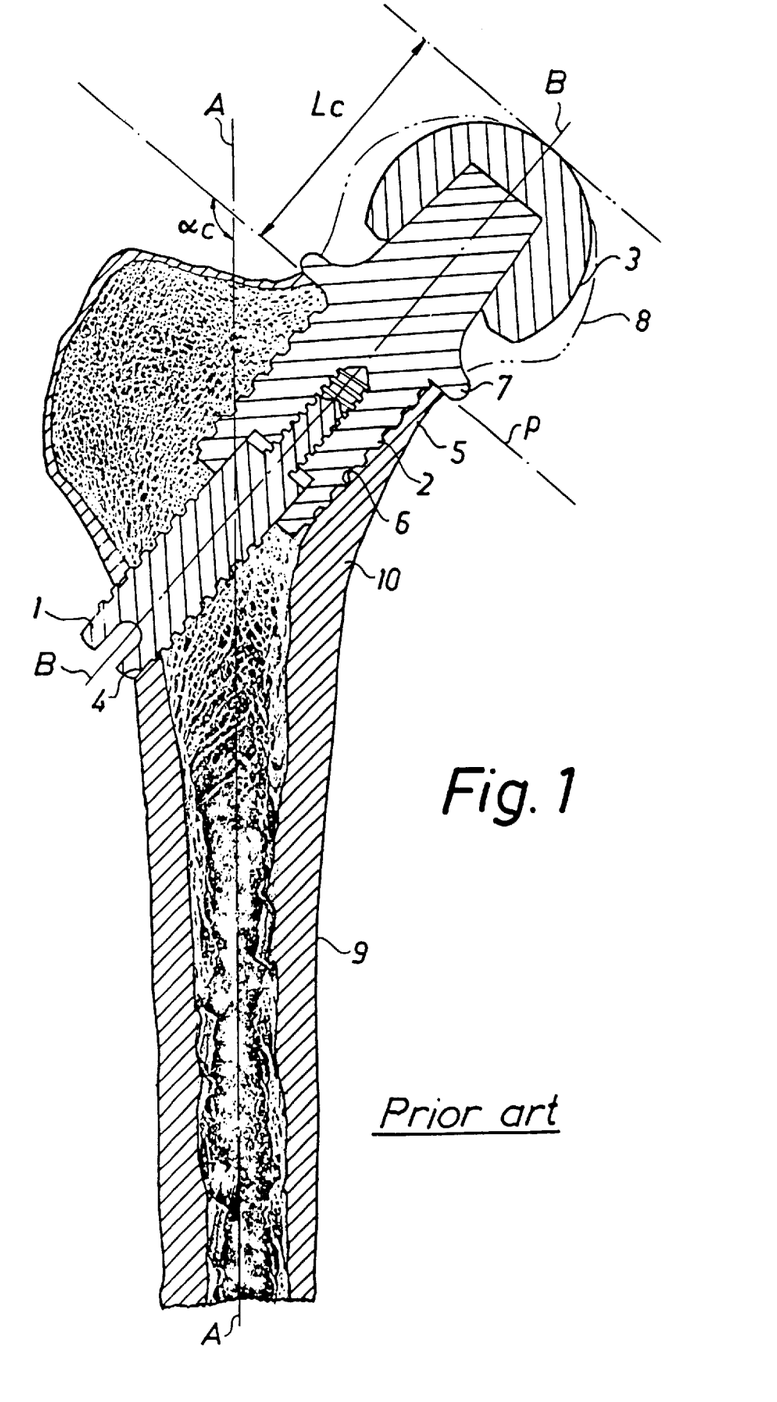
FIG. 1 is sectional view of a prior-art hip joint prosthesis anchored in the collum of a human femur.

WO 93/16663 discloses a hip joint prosthesis comprising an attachment part for a ball unit which is designed to be anchored in the neck of a human femur (collum femoris). The attachment part comprises a part for carrying a ball or caput intended to be attached to the collum after performing a resection of the head of the collum. The attachment part also comprises a fixture member comprising two main parts, a first part which is to extend through a bore hole from the collum towards the outer side of the femur and a second part intended to fit into a cylindrical cavity cut into the cancellous bone of the collum. A hip joint prosthesis of this kind is illustrated in FIG. 1 of the accompanying drawings. Further examples of prior-art hip joint prostheses are disclosed in WO 93/01769 and WO 89/11837.

In order to obtain a strong anchorage of the prosthesis, as discussed in general terms in WO 93/16663, the fixture member is preferably brought into engagement with the inside of the cortical bone in the collum as shown in FIG. 1, since such a contact with the cortical bone will reduce the risk of mechanical loosening of the prosthesis fixture member. In order to achieve this engagement, the sectioning or cutting plane P along which the head is to be removed must make an accurately determined cutting angle $\alpha_c$ with the main axis (A—A) of the femur. The specific value of this cutting angle for a patient is normally determined in advance from radiographs of the femur.

Furthermore, it is also essential that said cutting plane is selected at an accurately determined cutting level $L_c$ in relation to the proximal end of the collum head to be removed, in order that the patient should not limp. This cutting level can also be determined in advance from radiographs of the femur.

It is therefore an object of the invention to make it possible to perform a resection of the head of the femoral collum with high precision along a cutting plane at such a predetermined cutting angle and cutting level.

It is also an object of the invention to make it possible to perform such high-precision cutting in a quick and reliable manner.

A specific object of the invention is to provide a cutting guide instrument by means of which both the cutting angle and the cutting level can be determined in a reliable and accurate manner, and which can be used for guiding a cutting blade or the equivalent along the cutting plane thus established.

DISCLOSURE OF THE INVENTION

The above and other objects of the invention are achieved by a cutting guide instrument and method, as well as the use of such an instrument, having the features set out in the appended claims.

Thus, a cutting guide instrument according to the invention has a support part comprising a fixture member intended to be fixed to the femur during resection; a longitudinal guide carrier, which in use of the instrument is supported by the support part and extends along the femoral collum at said predetermined cutting angle $\alpha_c$ to the femoral shaft; and a cutting guide, which is supported by and is movable along the axis of the guide carrier to a cutting position corresponding to the predetermined cutting level $L_c$.

The instrument according to the invention is to be used subsequent to the determination of the cutting angle and the cutting level, and subsequent to the dislocation of the hip joint of the patient. The angle of the guide carrier relative to the femoral shaft will ensure that the cutting guide, and thus the cutting plane, will present the correct predetermined cutting angle relative to the femoral shaft irrespective of the cutting level. Proper adjustment of the longitudinal position of the cutting guide along the axis of the guide carrier ensures that the cutting plane will also be at the correct predetermined distance from the proximal end of the caput, i.e. on the correct cutting level.

According to a preferred embodiment of the invention, the guide carrier is pivotably supported by the support part for angular movement about a pivot axis extending transversely of a plane of symmetry of the femur, so as to allow adjustment of said cutting angle ($\alpha_c$) relative to the femoral shaft. In this context, the term "plane of symmetry of the femur" refers to a plane which divides the femur into two essentially equal, but mirrored halves. Such a pivotability of the guide carrier is advantageous in that it permits higher tolerances for the positioning and adjustment of the fixture member relative the femur.

In the above embodiment, in which the guide carrier is pivotably supported, the instrument may further comprise an angle-reference member, which is provided with a relatively long alignment part extending transversely of the pivot axis of the guide carrier, and which is pivotably connected to the support part for angular movement about the pivot axis of the guide carrier to an angular position in which the alignment part is essentially parallel to the femoral shaft. This embodiment has the advantage that the angle of the guide carrier relative to the femoral shaft can be adjusted with a high degree of accuracy to be equal to the cutting angle, since (i) the angle between the reference member and the patient, i.e. the femoral shaft, can be established with precision by using the relatively long alignment part for the angular positioning of the reference member, and (ii) the angle between the reference member and the guide carrier, both being mechanical parts of the instrument, can also be established with a high degree of accuracy.

The above embodiment of the invention, which comprises a pivotable angle-reference member having a relatively long alignment member, can be implemented in two different ways. In a first alternative, the angle between the alignment part and the guide carrier is fixed, whereas in a second alternative that angle is variable.

An instrument according to the first alternative may, for example, be provided with a set of interchangeable guide carriers, each having a different, fixed angle relative to its alignment part.

In an instrument according to the second alternative— variable angle between guide carrier and alignment part— the guide carrier and the angle-reference member may be made separately pivotable about the pivot axis of the guide carrier and be provided with cooperating angle-indicating means for visual indication of the value of the selected angle between the guide carrier and the alignment member. The angle of the guide carrier will then be adjusted in a two-stage operation. First, the angle-reference member is angularly positioned about the pivot axis by directing the alignment part thereof along the femoral shaft, e.g. by bringing a distal end of the alignment part in a position opposite to the corresponding knee-joint, preferably the patella. Next, the guide member is pivoted about the same pivot axis until the predetermined cutting angle is visually indicated by the angle-indicating means.

Generally, if the guide carrier is pivotable relative to the support part, the instrument is preferably provided with cutting-angle locking means for locking the guide carrier against pivotal movement about its pivot axis.

According to a preferred embodiment of the invention, the fixture member of the support part is in the form of a nail, which is intended to be temporarily anchored in the femur. Preferably, the nail is introduced in the upper part of the femur neck in a direction towards the femoral shaft, and by choosing a-sufficiently long nail, it can reach into and be guided by the femoral shaft in order to position the support part correctly relative to the femur.

For achieving a correct alignment of the guide carrier relative to the above-defined plane of symmetry of the femur, the support member may comprise a longitudinal collum-alignment member, such as a rod or slit-forming means, which is intended to be aligned with said plane of symmetry of the femur. As will be apparent from the following detailed description of a preferred embodiment of the invention, the use of a collum-alignment member is advantageous in that the cutting plane can be correctly and precisely oriented in two orthogonal directions, and thus not only in the direction corresponding to the cutting angle.

In order to position the cutting guide at a cutting level on a correct distance from the proximal end of the collum head, the guide carrier may be provided with an abutment arm, which protrudes transversely from the guide carrier and which is intended to be brought into abutment with the proximal end of the collum head. The guide carrier and the cutting guide should then be provided with cooperating position-indicating means for visual indication of the distance, along the axis of the guide carrier, between the cutting guide and the abutment arm, i.e. indication of when the cutting guide is positioned at the correct cutting level. Preferably, means are provided for locking the cutting guide on this cutting level against further movement along the axis of the guide carrier.

Normally, the instrument according to the invention is a separate instrument, which does not include the cutting tool itself. However, it is also envisaged that the cutting tool could be integrated in, supported by or be part of the cutting guide. If the cutting tool is separate from the cutting guide, the latter may be provided with a cutting slit for receiving and guiding a cutting blade or the equivalent.

A method according to the invention for enabling high-precision resection of the head (caput femoris) of the neck of a human femur (collum femoris) at a predetermined cutting angle $\alpha_c$ to the femoral shaft and on a predetermined cutting level $L_c$ with respect to the proximal end of the caput, is characterised by the steps of:

aligning a longitudinal guide carrier along the femoral collum at said predetermined cutting angle to the femoral shaft, providing a cutting guide, which is supported by and is movable along an axis of the guide carrier, and moving said cutting guide along the guide carrier to a cutting position corresponding to the predetermined cutting level.

Preferred modes of implementation of the inventive method are set out in the dependent claims.

The invention will now be illustrated in greater detail by an exemplary embodiment of a cutting guide instrument according to the invention and the use thereof, with reference to the accompanying drawings.

DETAILED DESCRIPTION OF A PREFERRED EMBODIMENT OF THE INVENTION

FIG. 1 illustrates a hip joint prosthesis of the type disclosed in WO93/16663, comprising a cylindrical first fixture part 1, a plug-like, cylindrical second fixture part 2 carrying a bail or caput 3. The first part 1 is fitted into a hole 4 drilled longitudinally through the femoral collum 5 along axis B—B. The second fixture part 2 is fitted into a cylindrical recess 6 cut in the collum 5 and co-axial with the drilled hole 4. The cylindrical part 2 has a circumferential flange 7 limiting its insertion into the recess 6, said flange 7 abutting a sectioning or cutting plane P along which the head 8 of the collum 5 has been removed by a cutting tool, as shown by dash-dot-lines.

The cutting plane P has been selected at a predetermined cutting angle $\alpha_c$ to the femoral shaft 9, the longitudinal main direction of which is identified by a straight line A—A in FIG. 1. Furthermore, the cutting plane P has been selected at a predetermined cutting level $L_c$ with respect to the proximal end of the head 8 of the collum 5.

Furthermore, and as can be seen from the sectional view in FIG. 1, the fixture parts 1, 2 of the prosthesis are so positioned and directed relative to the femur that an outer threaded cylindrical surface of the plug-like second fixture part 2 engages the inside of the cortical bone 10 at the transition part between the femoral collum 5 and the femoral shaft 9, whereby secure anchorage of the prosthesis is achieved.

A preferred embodiment of a cutting guide instrument according to the invention, and the use thereof for enabling the cutting along a cutting plane P as shown in FIG. 1, will now be described in detail with reference to FIGS. 2–8, illustrating the structure of the instrument and the subsequent steps to be taken, like parts in FIG. 1 and FIGS. 2–4 bearing like reference numerals.

Generally, the instrument according to the invention comprises a support part 11 to be fixed to the femur (FIGS. 2–4), a longitudinal guide carrier 12 supported by the support (FIGS. 5–8), and a cutting guide 13 movable along the axis C—C of the guide carrier 12 (FIGS. 5–8). These and other parts of the instrument can be made of any suitable, rigid material, such as stainless steel.

Figures 2, 3:
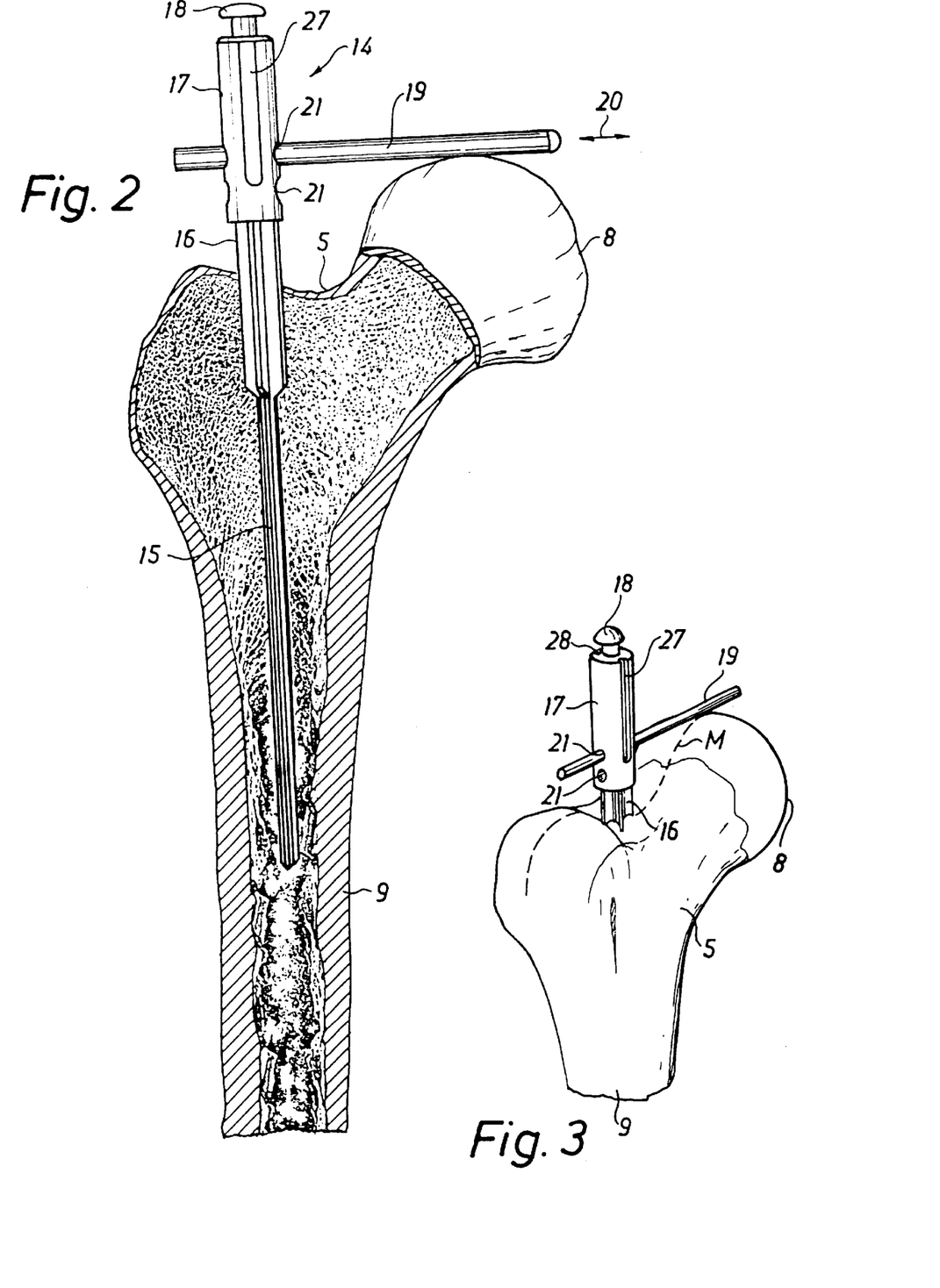
FIG. 2 is a part-sectional view illustrating the anchorage of a fixture member in the form of a nail in the femur.
FIG. 3 is a perspective view corresponding to FIG. 2, illustrating how the nail is oriented in relation to a plane of symmetry of the femur.

In the embodiment shown in the drawings, the support part 11 comprises as fixture member a nail 14 having a total length of about 18 cm. However, other types of fixture members can also be used, such as clamping means. The nail 14 comprises in its longitudinal direction the following four integrally formed portions 15–18: a relatively long and narrow end portion 15 having an essentially cross-shaped section and a width in the order of 5 mm; a relatively short and wide nail portion 16 also having an essentially cross-shaped section, but a width in the order of 10 mm; an essentially cylindrical connecting portion 17; and a flange-like top portion 18. The nail 14 is introduced in a direction substantially coinciding with the main axis A—A of the femoral shaft 9 and in an area near to or coinciding with fossa trochanterica. As shown in FIG. 2, the nail 14 is long enough for the end portion 15 to reach into and be guided by the interior of the femoral shaft 9, whereby any unintentional inclination of the nail 14 relative to the femur axis A—A will be essentially prevented, or at least essentially reduced, as the nail is introduced further into the femoral shaft. Depending on the size of the femur, a varying length of the wider nail portion 16 will be anchored in the collum 5.

As will be apparent from the following description, the rest of the support part of the instrument is to project essentially orthogonally from a plane of symmetry of the femur. Therefore, it is not only the inclination of the nail 14 relative to the femoral shaft 9 that is of importance, but also its orientation about its own longitudinal axis. For this reason, the connecting portion 17 of the nail 14 is provided with a longitudinal collum alignment member 19 in the form of a rod, which extends orthogonally from the connecting portion 17 about 7–10 cm. As shown in FIG. 3, the rod 19 is to be directed along a plane of symmetry M of the femoral collum 5. The precise direction should be established during the introduction of the narrower end portion 15 of the nail 14, since the anchorage of the wider nail portion 15 in the femoral collum 5 will effectively fix the angular orientation of the nail 14 about its own axis owing to the cross-shaped section of the nail portion 16.

As indicated at 20 in FIG. 2, the rod 19 is displaceable in its longitudinal direction in a diametrical through bore 21 in the connecting portion 17. Moreover, the rod 19 can be inserted into any of a number (only two in the illustrated embodiment) of such through bores 21. Which bore is to be chosen depends on the size and shape of the femur to be cut.

Figure 4:
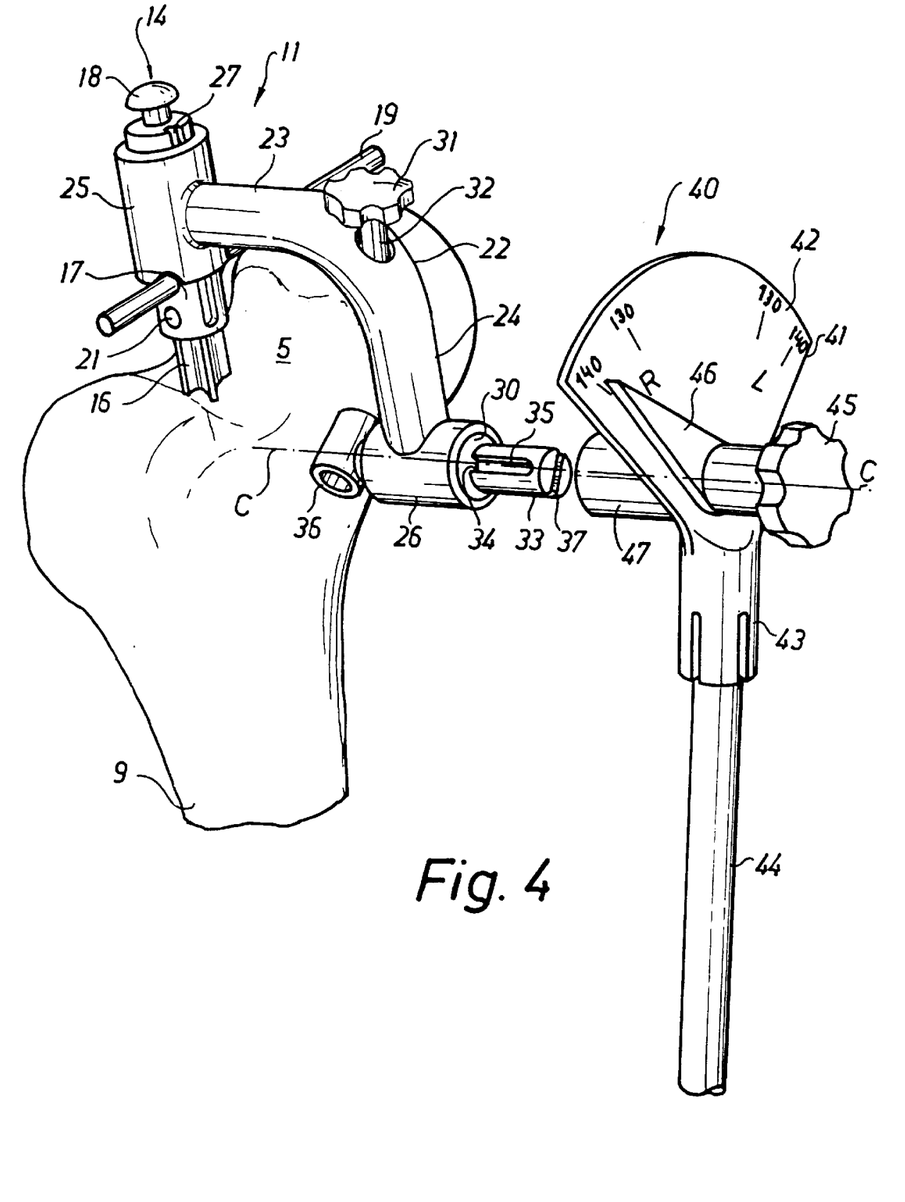
FIG. 4 is a perspective view illustrating the mounting of the support part to the nail in FIGS. 2 and 3.

The nail 14 now being anchored in the femur as shown in FIGS. 2 and 3, the rest of the support part 11 can be mounted on the connecting portion 17 as shown in FIG. 4. In this exemplary embodiment, the support part 11 further comprises a L-shaped cantilever 22 having a first arm 23 and a second arm 24 interconnected at right angles. The first and the second arms 23 and 24 are each provided with a cylindrical sleeve 25 and 26, respectively, the longitudinal direction of which extends in the plane of the L-shaped cantilever 22 and orthogonally to the respective arm. The sleeve 25 of the first arm 23 has an internal diameter corresponding to the outer diameter of the cylindrical connecting portion 17 and is provided with inwardly projecting tap means (not shown) to be received in longitudinal grooves 27, 28 formed in the connecting portion 17, in order to prevent rotation of the cantilever 22 about the nail 14. These tap means are so located relative to the pin 19 that the cantilever 22, when mounted on the nail 14, will project orthogonally from the plane of symmetry M, provided that the alignment rod 19 has been properly oriented as indicated in FIG. 3. As appears from FIG. 4, the selected bore 21 for the alignment rod 19 will determine the level of the sleeve 25 relative to the nail 14, and thus the level of the other sleeve 26 relative to femoral collum 5.

The sleeve 26 of the second arm 24, the axis of which coincides with a pivot axis C—C for the longitudinal guide carrier 12 (FIG. 4) and which is normally positioned close to the intersection of axis A—A and axis B—B in FIG. 1, carries an internal, cylindrical bearing member 30 having an outer cylindrical diameter that corresponds to the internal diameter of the sleeve 26. The bearing member 30 is thus freely rotatable inside the sleeve 26 about the pivot axis C—C, but can be locked relative to the sleeve 26 by the use of angle-locking means. In this embodiment, these angle-locking means comprise a hand knob 31, a threaded spindle 32 extending inside the arm 26, and means (not shown) located near the sleeve 26 for blocking rotational movement of the bearing member 30 when the spindle 32 is turned by the knob 31. The selected angular position of the bearing member 30 will determine the cutting angle $\alpha_c$.

The rotatable bearing member 30 has a longitudinal channel for slidably receiving a rod-shaped, cylindrical pivot shaft 33. The pivot shaft 33 is freely displaceable relative the bearing member 30 in the direction of the pivot axis C—C, whereas relative rotational movement of these two parts is prevented by two opposite ridges 34, which project radially inwardly from the channel of the bearing member 30 and which slidingly engage corresponding opposite grooves 35 formed in the pivot shaft 33. This arrangement allows for adjustment of the distance between the guide carrier 12 and the collum 5 even after locking of the cutting angle by the knob 31.

The end of the pivot shaft 33 facing the femoral collum 5 is integrally connected to a cylindrical sleeve 36 for receiving the rod-shaped guide carrier 12. The opposite end surface of the pivot axle 31 is provided with a coupling slit 37.

Subsequent to the mounting of the cantilever 22 to the nail 14 as shown in FIG. 4, but before locking the cutting angle $\alpha_c$, an angle-reference member 40 also shown in FIG. 4 is temporarily mounted on the end of the pivot shaft 33 provided with the coupling slit 37. The purpose of the angle-reference member 40 is to establish an exact angle reference relative to the main axis A—A of the femoral shaft 9, and to provide means for convenient adjustment of the instrument to the predetermined value of the cutting angle. To this end, the angle-reference member 40 comprises two parts which are mutually rotatable along an axis coinciding with the pivot axis C—C. The first part, which is intended to be oriented relative to the femoral shaft 9, comprises an essentially sector-shaped protractor 41, having two sets of cutting angle values 42 for right and left femurs, respectively, a cylindrical connecting part 43, and a relatively long alignment part in the form of a rod 44, releasably connected to the connecting part 43 and extending transversely of, in this embodiment orthogonally to, the pivot axis C—C. Preferably, the alignment rod 44 is long enough to reach the knee-joint. The second part of the angle-reference member 40, which is intended to be rotationally fixed to the pivot shaft 33 by means of the coupling slit 37, comprises an angle-adjustment knob 45 and a cutting angle-indicator 46 on the angle-indication side of the protractor 41, and a cylindrical connecting bushing 47 arranged on the opposite side of the protractor 41. The bushing 47 is provided with an internal protrusion (not shown) for engaging with the coupling slit 37. These three parts 45, 46 and 47 are thus rotatable as a unit in relation to the protractor 41.

When the angle-reference member 40 has been mounted on the pivot shaft 33 of the cantilever 22, the protractor 41 is brought into a reference position relative to the femur by turning the alignment rod 44 into a position where the distal end thereof (not shown) is located opposite to the centre of the patella. Thereafter, and with the rod 44 held stationary in said reference position over the knee-joint, the cutting angle $\alpha_c$ is set by turning the knob 45 until the indicator 46 is at the correct, predetermined angle value 42, e.g. 140°, whereby the axis of the sleeve 36 will be exactly directed in the predetermined cutting angle relative to the femoral shaft 9. The cutting angle can now be fixed by locking the bearing member 30 relative to the sleeve 26 by means of the knob 31. The angle-reference member 40 can then be removed from the cantilever 22. Obviously, it is also possible to set the angle value before mounting the angle indication member 40.

Figure 5:
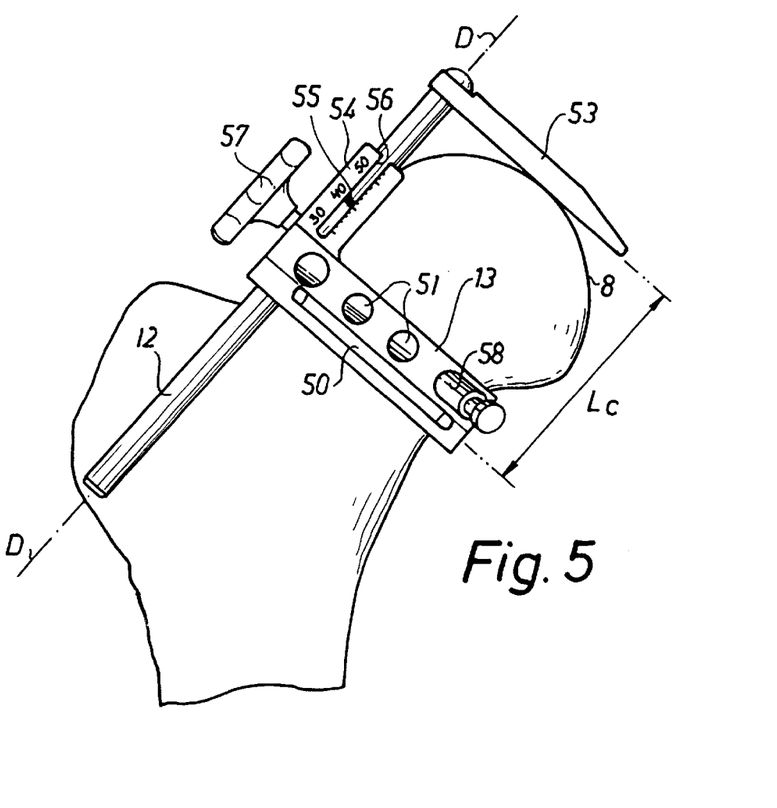
FIG. 5 is a front view of a cutting guide mounted on a guide carrier, illustrating the adjustment of a cutting level.
Figure 6:
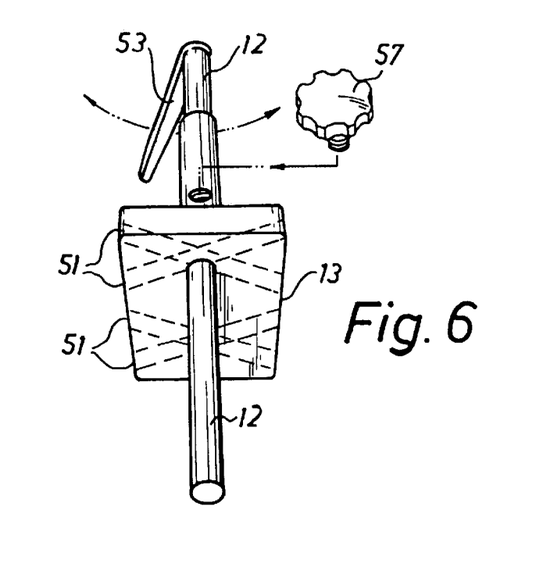
FIG. 6 is a bottom perspective view corresponding to FIG. 5.
Figures 7, 8:
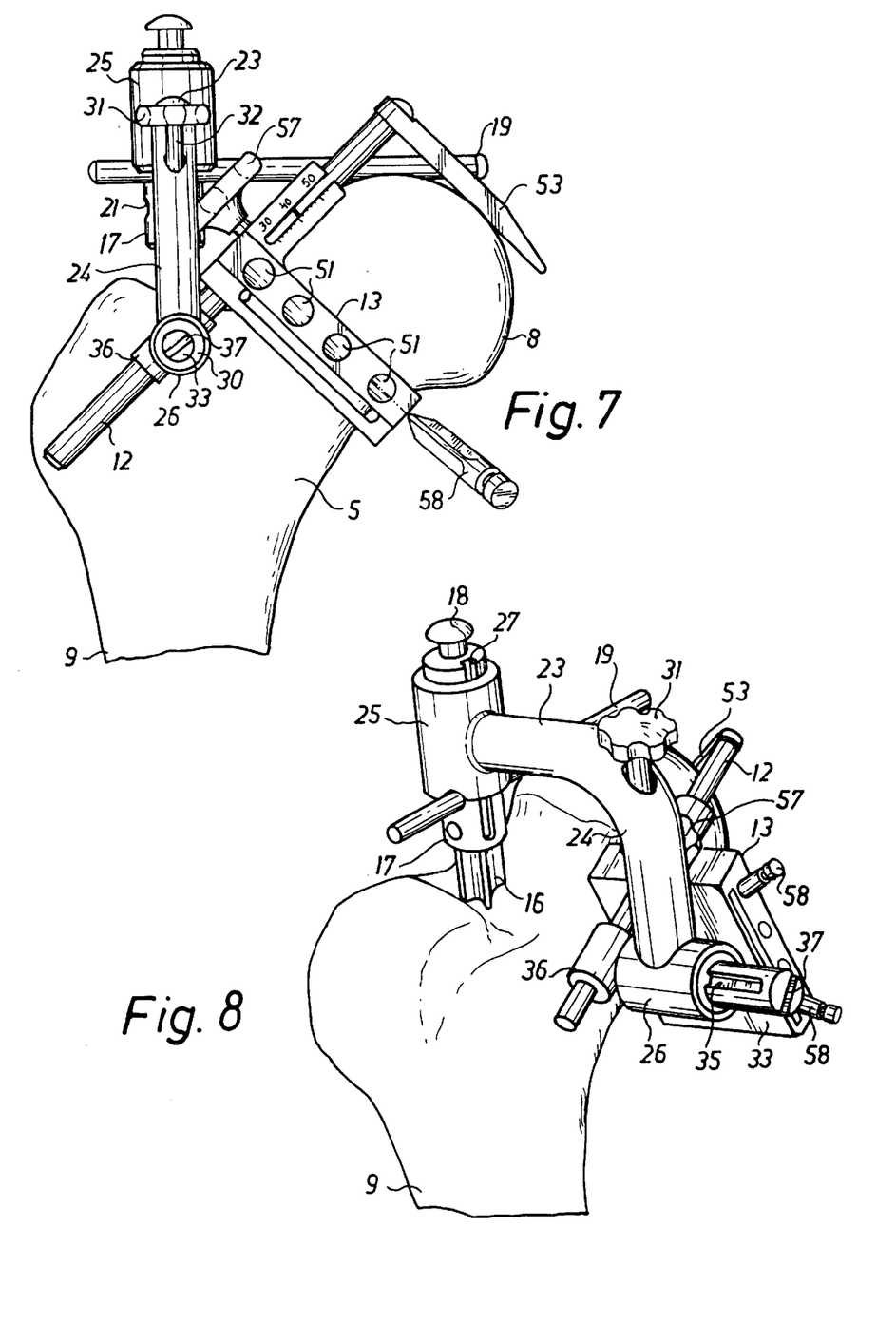
FIG. 7 is a front view of the instrument with the cutting guide in cutting position.
FIG. 8 is a rear perspective view corresponding to FIG. 7 with the cutting guide anchored by two nails.

Reference is now made to FIGS. 5 and 6, which illustrate the adjustment of the cutting level $L_c$. In this embodiment, the cutting guide 13 is in the form of a rectangular block provided with a cutting slit 50 and four anchoring channels 51, intersecting each other two by two as shown in FIG. 6. The cylindrical guide carrier 12 is received and freely movable in a bore provided in the cutting guide 13 orthogonally to the plane of the cutting slit 50. At its proximal end 54 the guide carrier 12 is provided with an abutment arm 53, extending transversely to the axis D—D of the guide carrier 12 and being intended to be brought into abutment with the proximal end of the caput 8 to be removed, as shown in FIG. 7. In this embodiment, the abutment arm 53 is rotatably supported by the guide carrier 12.

Preferably before inserting the guide carrier 12 in the sleeve 36, the distance between the cutting slit 50 and the abutment arm 53 is set equal to the predetermined cutting level $L_c$, as shown in FIG. 5. In this embodiment, the setting of the cutting level is achieved by means of level-indicating means in the form of a slit ruler 54 mounted on the cutting guide 13 and an indication ring 55 visible through the slit 56 of the ruler 54. When the cutting level has been set to the predetermined value $L_c$, the cutting guide 13 is locked in relation to the guide carrier 12 by a turnable locking knob 57.

The unit shown in FIG. 5, now being locked at the predetermined cutting level, is connected to the cantilever 22 as shown in FIG. 7 by inserting the free end of the guide carrier 12 into the fixed sleeve 36 until the abutment arm 53 engages the proximal end of the caput 8. The cutting slit 50 will then define a cutting plane P having the predetermined cutting angle and cutting level.

Increased precision can be obtained if the cutting guide 12, as suggested in the embodiment shown, is anchored in the caput 8 before performing the resection. This is done by first pivoting the cutting guide 13 and the guide carrier 12 in relation to the sleeve 26 about the axis D—D, in combination with displacement of the pivot shaft 33 relative to the locked bearing member 30, until the cutting guide 13 is brought into contact with the femoral collum 5. Thereafter, two anchoring nails 58 are inserted through two of the channels 51 of the cutting guide 12 and anchored in the part of the collum to be removed. The situation is now as depicted in FIG. 8.

The adjustment and anchorage of the instrument being now completed, the cutting operation can be performed by inserting a cutting blade or the equivalent (not shown) through the cutting slit 50, which will effectively guide the cutting blade with a high degree of accuracy along the predetermined cutting plane P. When resection has been performed, the instrument is removed from the femur by retracting the nail 14.

As an alternative to the situation illustrated in FIG. 2, the nail 14 may be introduced at the trochanter major instead, i.e. further to the left in FIG. 2. As will be seen from FIG. 7, such a positioning of the nail 14 would result in a higher degree of movability of the cutting guide 13 relative to the guide carrier 12.

Figure 9:
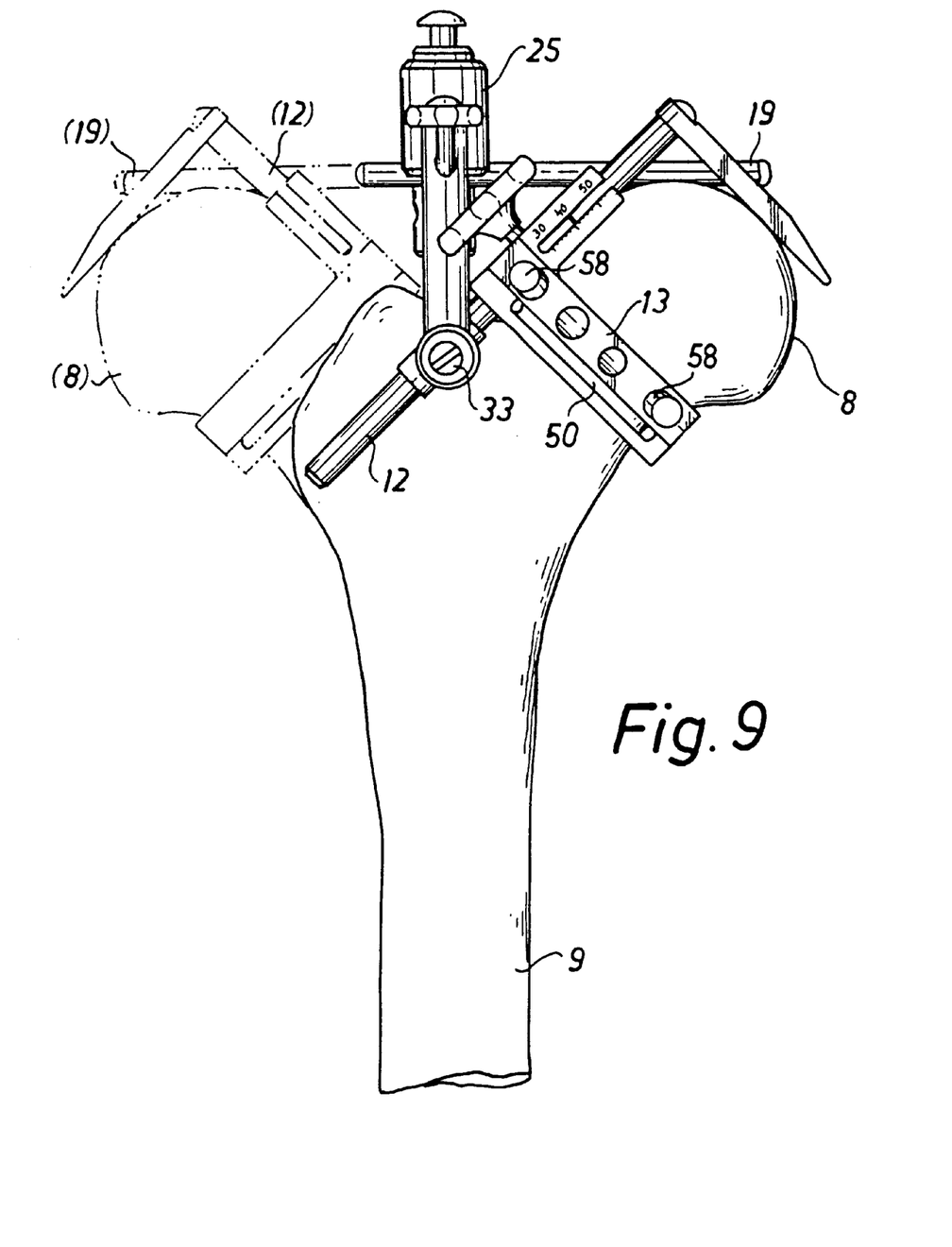
FIG. 9 is a side view corresponding to FIGS. 7 and 8, but illustrating by dash-dot-lines right-hand and left-hand use of the instrument.

Finally, FIG. 9 illustrates how the instrument described above can be used for the right or the left femur.

What is claimed is:

1. A cutting guide instrument for enabling high-precision resection of the head (caput femoris) of the neck of a human femur (collum femoris) at a predetermined cutting angle to the femoral shaft and on a predetermined cutting level with respect to the proximal end of the caput, said cutting guide comprising:

a support part, comprising a fixture member intended to be fixed to the femur during said resection;

a longitudinal guide carrier, having a longitudinal axis, which in use of the instrument is supported by the support part with the longitudinal axis extending along the femoral collum at a predetermined alignment angle to the femoral shaft; and a cutting guide, which in use of the instrument is supported by and can be positioned along the axis of the guide carrier at a cutting position corresponding to the predetermined cutting level, wherein the longitudinal guide carrier and the cutting guide are adapted such that when the cutting guide is supported by the longitudinal guide carrier at the cutting position, the cutting guide is oriented at the predetermined cutting angle to the femoral shaft, and wherein the cutting guide is pivotable in relation to the axis of the guide carrier.

2. An instrument according to claim 1, wherein the guide carrier is displaceable transversely of the support part in a direction parallel to its pivot axis, in order to adjust the distance between the cutting guide and the femoral collum.

3. An instrument according to claim 1, further comprising cutting guide locking means for locking the cutting guide against movement along the axis of the guide carrier.

4. An instrument according to claim 1, wherein the cutting guide is intended to be anchored in its cutting position to the part of the femur which is to be removed.

5. An instrument according to claim 4, wherein the cutting guide is provided with one or more channels for receiving anchoring means for enabling anchorage of the cutting guide.

6. An instrument according to claim 1, wherein the fixture member of the support part is in the form of a nail, which is intended to be temporarily anchored in the femur.

7. An instrument according to claim 6, wherein the nail (14) is intended to be introduced in the upper part of the femur neck (at fossa thochanterica) in a direction towards the femoral shaft (9), the length of the nail (14) being sufficient for the nail to reach into and be guided by the femoral shaft (9).

8. An instrument according to claim 1, wherein the support part further comprises a cantilever, which is releasably connected to the fixture member at a first end portion and which supports the guide carrier at a second end portion.

9. An instrument according to claim 1, wherein the support part further comprises a collum-alignment member which is intended to be aligned in parallel with a plane of symmetry of the femoral collum, in order to direct the guide carrier in a direction parallel to said plane of symmetry.

10. An instrument according to claim 1, wherein the guide carrier is provided with an abutment arm, which protrudes transversely from the guide carrier and which is intended to be brought into abutment with the proximal end of the caput, and wherein the guide carrier and the cutting guide are provided with cooperating position-indicating means for visual indication of the distance between the cutting guide and the abutment arm along the axis of the guide carrier.

11. An instrument according to claim 10, wherein the guide carrier (12) is movable in its longitudinal direction in relation to the support part (11) for bringing the abutment arm (53) into abutment with the proximal end of the caput (8).

12. An instrument according to claim 1, wherein the cutting guide is provided with a cutting slit for receiving and guiding a cutting blade or the equivalent.

* * * * *